United States Patent [19]
Schweiger

[11] Patent Number: 6,040,190
[45] Date of Patent: Mar. 21, 2000

[54] METHOD FOR DETERMINING THE CONCENTRATION C OF AN ABSORBENT HOMOGENEOUSLY DISTRIBUTED IN A CARRIER

[75] Inventor: Gerd Schweiger, Graz, Austria

[73] Assignee: AVL Medical Instruments AG, Schaffhausen, Switzerland

[21] Appl. No.: 08/843,294

[22] Filed: Apr. 14, 1997

Related U.S. Application Data

[63] Continuation of application No. 08/458,844, Jun. 2, 1995, abandoned.

[51] Int. Cl.$^7$ ........................... G01N 21/00
[52] U.S. Cl. ................ 436/164; 436/167; 436/171; 436/177
[58] Field of Search ................. 436/164, 167, 436/168, 171, 177

[56] References Cited

U.S. PATENT DOCUMENTS

| | | | |
|---|---|---|---|
| 4,937,186 | 6/1990 | Siddiqi et al. | 435/28 |
| 5,208,136 | 5/1993 | Zanoni et al. | 430/290 |
| 5,224,197 | 6/1993 | Zanoni et al. | 385/130 |

OTHER PUBLICATIONS

Skoog, Douglas Arvid, 1918, Principles of Instrument Analysis, 1985 by CBS College Publishing, pp. 160–168, 208–216, 277–288, 303–304, and 351–352.

*Primary Examiner*—Lyle A. Alexander
*Attorney, Agent, or Firm*—Watson Cole Grindle Watson, P.L.L.C.

[57] ABSTRACT

For the purpose of determining the concentration c of an absorbing medium distributed homogeneously in a carrier, even if the film thickness d of the carrier is unknown, an absorbing medium is used whose measured absorption $a(\lambda)$ deviates from Lambert-Beer's law, in particular in the region of higher concentration, and $n \geq 2$ model components of the absorbing medium are assumed, so that $$a(\lambda) = (\epsilon_1(\lambda).c_1 + \epsilon_2(\lambda).c_2 + \ldots \epsilon_n(\lambda).c_n).d.$$

The absorption $a(\lambda_i)$ is measured for at least n wavelengths, and the spectral absorption values $\epsilon_i(\lambda_i)$ and concentrations $c_i$ of the model components are computed and the concentration c is determined from the functional relationship between the concentration c and concentrations $c_i$ of the model components $c = f(c_i)$, which relationship is obtained by calibrating measurements.

15 Claims, 2 Drawing Sheets

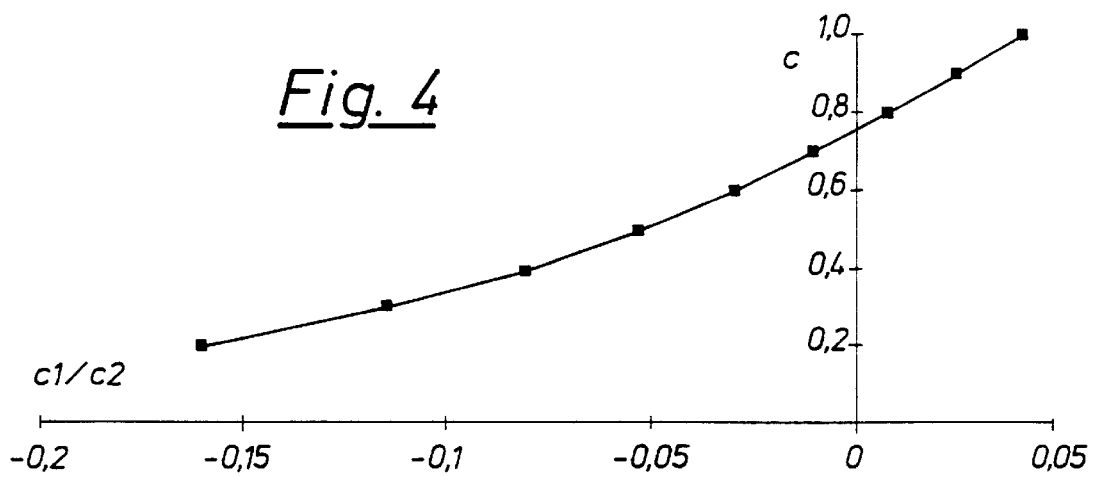

METHOD FOR DETERMINING THE CONCENTRATION C OF AN ABSORBENT HOMOGENEOUSLY DISTRIBUTED IN A CARRIER

CROSS-REFERENCE TO RELATED APPLICATION

This application is a continuation of application Ser. No. 08/458,844, filed Jun. 2, 1995, now abandoned.

BACKGROUND OF THE INVENTION

The invention relates to a method for determining the concentration c of an absorbent homogeneously distributed in a carrier, in which the absorption $a(\lambda)$ of the absorbent is measured while the value of spectral absorption $\epsilon(\lambda)$ is known, using Lambert-Beer's law $a(\lambda)=\epsilon(\lambda).c.d$ as a basis.

In a variety of applications it is necessary to determine the concentration c of a substance by means of an absorption measurement. Departing from Lambert-Beer's law $$a(\lambda)=\epsilon(\lambda).c.d$$

the concentration c is computed from the absorption measurement $a(\lambda)$, the spectral absorption curve $\epsilon(\lambda)$ and the film thickness d being known.

On the other hand it is often necessary in such applications that the film thickness d be calibrated or at least checked at regular intervals, as any error would have its direct effects on the computed value calculated of the concentration c. Such calibrations or checks are usually performed with the use of a medium whose concentration and spectral absorption behavior are fully known.

Series production of such a calibrating medium therefore requires extreme precision in the fabrication process, which cannot always be achieved at a reasonable cost. Instead, every batch is carefully measured before leaving the production plant, and the target values obtained are noted on an enclosed data sheet. In this instance the responsibility for adequate calibration of the equipment rests with the user. The disadvantage of this method is that a number of new sources of error are introduced, such as enclosing a wrong data sheet in the instance of different batches, reading errors, wrong input data, etc.

DESCRIPTION OF THE PRIOR ART

The known procedures and measuring devices described below, which utilize Lambert-Beer's law to obtain the concentrations of individual sample components by measuring the absorption of the sample, are characterized by the disadvantages mentioned above, necessitating in every instance knowledge and regular calibration of the exact film thickness of the sample.

In AT-E 56 271, for example, a method for determining the concentrations of haemoglobin derivatives in whole blood is described, which differs from conventional multi-component analyses in that sample turbidities due to leucocytes, excess blood lipids, erythrocytes, etc., can be taken into account.

A similar type of multi-component analysis is disclosed in DE-A 42 03 587. The components in a sample are determined on the basis of the absorption capacity at fixed wavelengths in the absorption spectrum of the sample. In this context a hypothetical matrix is prepared beforehand for the purpose of determining concentrations, using a combination of reference spectra for a number of components whose concentrations are known. The concentrations of the components to be measured are computed with the use of this matrix, which will permit quantitative analysis to be performed at great precision within a very short time.

In the method described in CH-A 637 767, finally, the concentrations of substances are measured by adding a first indicator to the sample, which will respond to a change in the concentration of a substance to be measured by a spectral change, and by further adding a reference indicator, which will change the measurement light but will not be changed by the concentration of the substance to be measured. As mentioned before, all known methods require accurate knowledge of the measured film thickness.

SUMMARY OF THE INVENTION

It is an object of the invention to propose a method for determining the concentration of an absorbent distributed homogeneously in a carrier, which will avoid the above disadvantages and which, in particular, will not necessitate accurate knowledge of the film thickness of the sample to be measured.

In the invention this is achieved by employing, in the absence of a known value for the film thickness d of the carrier, an absorbent whose measured absorption $a(\lambda)$ deviates from Lambert-Beer's law, in particular in the region of higher concentration, and by assuming $n \geq 2$ model components of the absorbent, so that $$a(\lambda)=(\epsilon_1(\lambda).c_1+\epsilon_2(\epsilon).c_2+\ldots \epsilon_n(\lambda).c_n).d,$$

and by measuring the absorption $a(\lambda_i)$ for at least n wavelengths, and by computing the spectral absorption values $\epsilon_i(\lambda_i)$ and concentrations $c_i$ of the model components, and, further, by determining the concentration c from the functional relationship between the concentration c and concentrations $c_i$ of the model components $c=f(c_i)$, which relationship is obtained by calibrating measurements.

With the method of the invention it is also possible of course to determine the film thickness d of the carrier without knowing the concentration c of the absorbent distributed in the carrier.

In preferred variants of the invention the proposal is put forward that the classes of substances indicated in the table below, or rather, their typical representatives are used as absorbents.

| Class | Representatives |
| --- | --- |
| Triphenylmethane dyes | rhodamine |
| | sulforhodamine |
| | crystal violet |
| | fluorescein |
| Azo dyes | butter yellow |
| | Bismarck brown (vesuvin) |
| Quinonoid dyes | anthraquinone |
| | naphthoquinone |
| | indanthrene |
| Porphyrins and phthalocyanines | oxazole |
| Cyanines | merocyanine |
| Polycyclic aromatic | decacyclene |
| Hydrocarbons | perylene |
| | naphthacene |
| Indigo dyes | indigo |

DESCRIPTION OF THE DRAWINGS

Following is a more detailed description of the invention as illustrated by the accompanying drawings, in which.

DETAILED DESCRIPTION OF THE INVENTION

Figure 1:
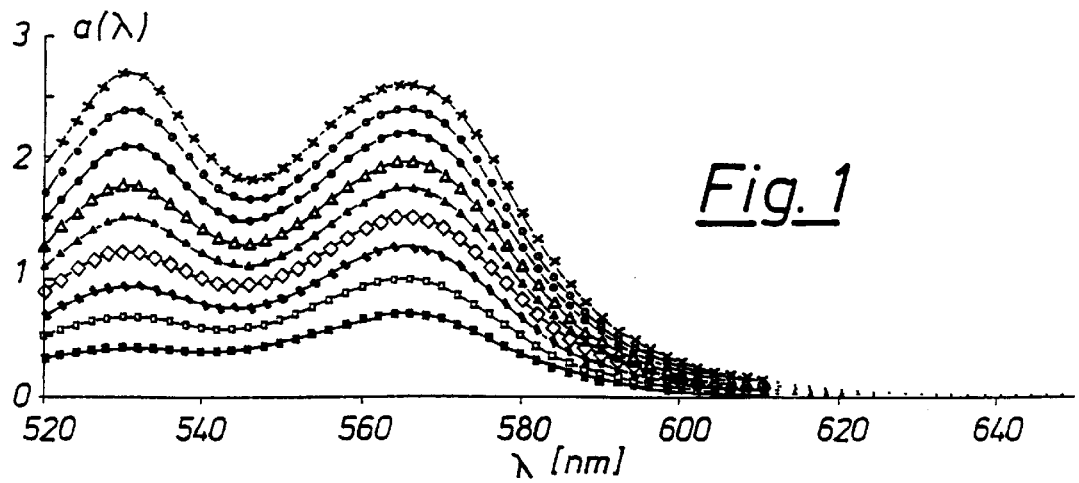
FIG. 1 shows absorption spectra of calibrating solutions with different concentrations, FIG. 2 the reference spectra for a two-component system, FIG. 3 a diagram of the fictitious components $c_1$, $c_2$, plotted over the weighed concentration c, and FIG. 4 the functional relationship between the absolute concentration c and the quotient of the hypothetical concentrations $c_2$ and $c_1$.

Various dyes, such as sulforhodamine B, show deviations from Lambert-Beer's law, especially in the region of higher concentrations. These deviations are characterized in that the measured absorption $a(\lambda)$ does not rise in direct proportion to the concentration of the absorbing substance. FIG. 1 gives the absorption curves from 520 to 640 nm for nine different concentrations of the high-purity basic substance, which are represented by different graphic symbols.

Figure 2:
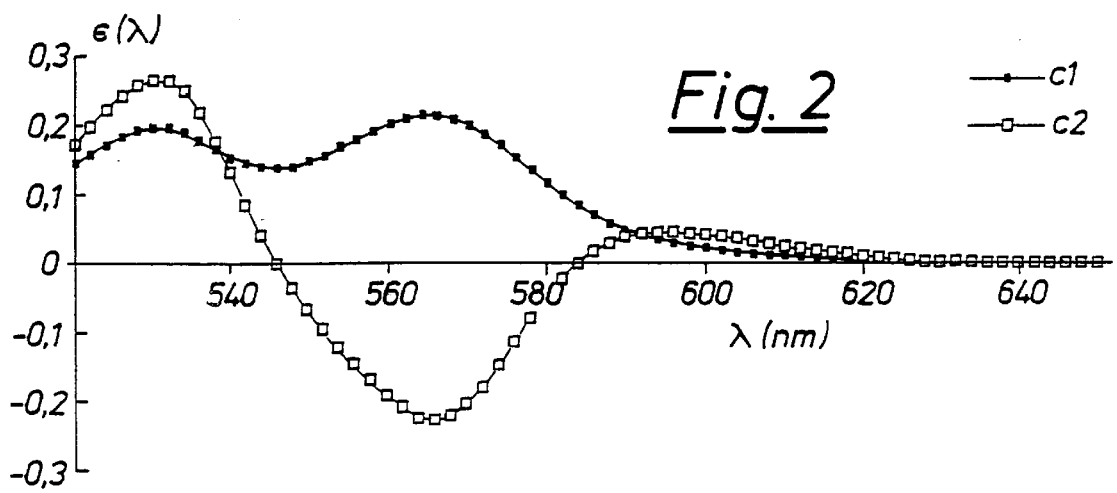

It is obvious even to the naked eye that the left peak seems to grow more "rapidly" than the right. For this reason the entire family of curves cannot be described satisfactorily by a single component $$a(\lambda)=\epsilon(\lambda).c.d$$

even if there is only one basic substance. This image will be completely changed if a description with n fictitious components $$a(\lambda)=(\epsilon_1(\lambda).c_1+\epsilon_2(\lambda).c_2+\ldots \epsilon_n(\lambda).c_n).d.$$

is chosen. By means of mathematical procedures (such as Singular Value Decomposition) it is possible to compute the spectral absorption curves $\epsilon(\lambda)$ of the individual fictitious components which are orthogonal to each other. For the sake of simplicity and without implying restrictions on the general case, the example of a two-component system, i.e. n=2, is described below (see reference spectra FIG. 2).

For this system the concentrations of the individual components are determined by means of the known methods of multi-component analysis, the assumption being that the number of measuring wavelengths $m \geq n$.

Figure 3:
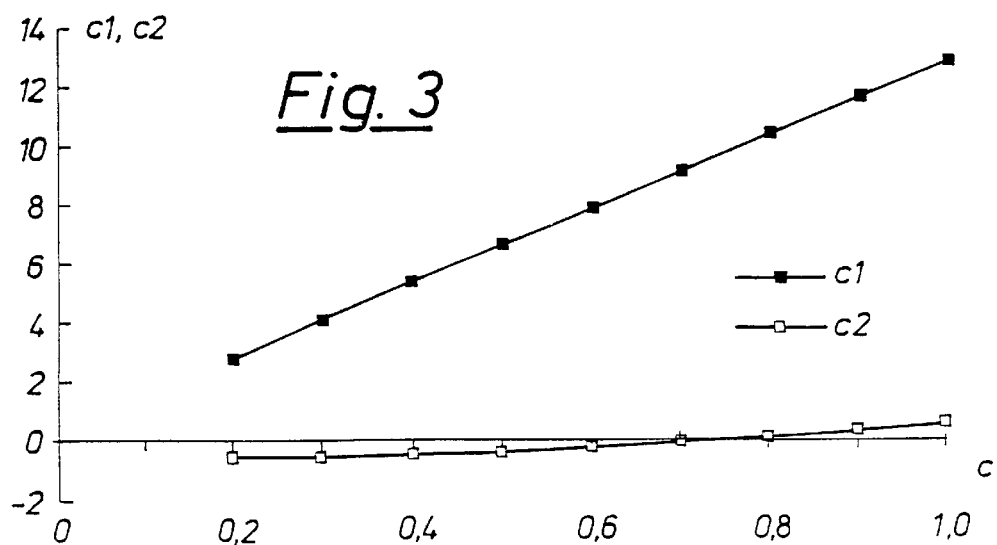

If we analyze the data in more detail we will find that the two fictitious components $c_1$ and $c_2$ do not occur independently of each other, but that quite the reverse is true; if we determine the concentrations $c_1$ and $c_2$ for the dilution series and if we enter them as functions of the weighed concentration c of the basic substance, we obtain the diagram as in FIG. 3.

Each concentration $c_1$ thus goes with a precisely defined concentration $c_2$, the quotient $c_2/c_1$, for example, being independent of the actual film thickness and containing only the information on the absolute concentration c of the basic substance. The functional relationship $c=f(c_2/c_1)$ is shown in FIG. 4.

In practice this function could be represented by a polynomial, a table or similar means.

The information on the actual film thickness is contained in the computed concentrations $c_1$ and $c_2$. Assuming that the reference spectra were obtained with the normal film thickness do being precisely known, we have a uniquely defined function $c_1=g(c)$, which describes the relationship between the concentration of the basic substance c and the corresponding concentration $c_1$. A deviation of the computed concentration $c_1$ from the expected value thus is directly proportional to the deviation of film thickness from the normal value do. We have $$\frac{d_{act}}{d_o} = \frac{c_1 \text{ measured}}{c_1 \text{ expected}}$$

with
- $d_{act}$ ... actual film thickness
- $d_o$ ... normal film thickness
- $c_1$ measured ... result of the multi-component analysis
- $c_1$ expected ... from the function $c_1=g(c)$ with $c=f(c_2/c_1)$ This will open up the, at first sight surprising, possibility of calibrating the film thickness of a cuvette with a dye of unknown concentration. This method may be implemented as a fully automatized procedure, i.e., without any interference by the user, so that the errors mentioned at the beginning of this paper are avoided.

I claim:

1. A method of spectroscopically determining the concentration c of a sample of a nonlinear absorbent that does not conform to Lambert-Beer's law and so exhibits a non-linear relationship between concentration and absorption, the method comprising:

(a) forming a mathematical model of said nonlinear absorbent, said model including a plurality n, $n \geq 2$, of model components each of which conforms to Lambert-Beer's law, the step of forming the mathematical model comprising:

(i) taking calibration spectroscopic data of absorption $a(\lambda)$ at the plurality n of wavelengths $\lambda$ for each of a plurality of calibration samples of said non-linear absorbent, said calibration samples having known concentrations; and (ii) from the calibration spectroscopic data taken in step (a)(i), determining parameters of the plurality of model components that would allow the plurality of model components to model the non-linear absorbency behavior of said absorbent by satisfying the following equation:

$$a(\lambda)=(\epsilon_1(\lambda) \cdot c_1+\epsilon_2(\lambda) \cdot c_2+ \cdots \epsilon_n(\lambda) \cdot c_n) \cdot d$$

where each model component $\epsilon_i(\lambda) \cdot c_i$, $1 \leq i \leq n$, has a spectral absorption value given by $\epsilon_i(\lambda)$ and a concentration $c_i$; and (b) applying the mathematical model to the sample of the absorbent, the step of applying the mathematical model comprising:

(i) taking measurement spectroscopic data for a sample of said absorbent of unknown concentration at the plurality n of wavelengths;

(ii) applying the equation set forth in (a)(ii) to said measurement spectroscopic data to determine the concentration values $c_i$ of the plurality of model components corresponding to the measurement spectroscopic data; and (iii) from the concentration values $c_i$ of the plurality of model components, calculating C.

2. A method according to claim 1, wherein step (b) further comprises computing a film thickness (d) of the sample of the absorbent from said concentrations $c_i$ of said fictitious components derived in step (b)(ii).

3. A method according to claim 1, wherein said absorbent is selected from the group consisting of triphenylmethane dyes.

4. A method according to claim 1, wherein said absorbent is selected from the group consisting of rhodamine, sulforhodamine, crystal violet and fluorescein.

5. A method according to claim 1, wherein said absorbent is selected from the group consisting of azo dyes.

6. A method according to claim 1, wherein said absorbent is selected from the group consisting of butter yellow and Bismarck brown.

7. A method according to claim 1, wherein said absorbent is selected from the group consisting of quinonoid dyes.

8. A method according to claim 1, wherein said absorbent is selected from the group consisting of anthraquinone, naphthoquinone and indanthrene.

9. A method according to claim 1, wherein said absorbent is selected from the group consisting of porphyrins and phthalocyanines.

10. A method according to claim 1, wherein said absorbent is selected from the group consisting of cyanines.

11. A method according to claim 1, wherein said absorbent is selected from the group consisting of oxazole and merocyanine.

12. A method according to claim 1, wherein said absorbent is selected from the group consisting of polycyclic aromatic hydrocarbons.

13. A method according to claim 1, wherein said absorbent is selected from the group consisting of decacyclene, perylene and naphthacene.

14. A method according to claim 1, wherein said absorbent is selected from the group consisting of indigo dyes.

15. A method according to claim 1, wherein said absorbent is indigo.

* * * * *